United States Patent [19]

Bochner

[11] 4,235,964

[45] Nov. 25, 1980

[54] METHOD FOR TESTING AND IDENTIFYING MICROORGANISMS

[76] Inventor: Barry R. Bochner, 1618 Sherman St., Alameda, Calif. 94501

[21] Appl. No.: 946,884

[22] Filed: Sep. 28, 1978

Related U.S. Application Data

[63] Continuation-in-part of Ser. No. 773,879, Mar. 3, 1977, Pat. No. 4,129,483.

[51] Int. Cl.$^2$ .............................................. C12Q 1/04
[52] U.S. Cl. ...................................... 435/34; 435/253; 435/38
[58] Field of Search ................ 435/34, 243, 253, 801, 435/35, 36, 37, 38

[56] References Cited
U.S. PATENT DOCUMENTS 4,129,483   12/1978   Bochner ................................. 435/34

Primary Examiner—Robert J. Warden

Attorney, Agent, or Firm—Reising, Ethington, Barnard, Perry & Brooks

[57] ABSTRACT

In accordance with the invention there is provided a method for identifying or testing an anaerobic microorganism wherein an aqueous suspension of a culture of the microorganism having a culture density of about $2 \times 10^8$ cells/ml, is brought into contact with an aqueous solution containing an oxidation-reduction indicator which substantially irreversibly undergoes a change in color upon being reduced and a biodegradable test substrate compound which, when catabolized by a microorganism, will engender reduction of the indicator, said aqueous suspension containing nutrient in a concentration sufficient to support microorganism culture growth without engendering reduction of the indicator when said suspension contacts said solution, and said suspension also containing a compound which reduces $O_2$ but does not reduce the indicator.

3 Claims, 4 Drawing Figures

METHOD FOR TESTING AND IDENTIFYING MICROORGANISMS

This patent application is a continuation-in-part of United States patent application Ser. No. 773,879 filed Mar. 3, 1977, now U.S. Pat. No. 4,129,483.

The subject matter of the present invention is a method for testing or identifying microorganisms by way of a colorimetric change brought about by reduction of a compound which constitutes one of the ingredients of the test compositions used.

BACKGROUND OF THE INVENTION

In studies concerning taxonomic classification, genetic analysis, or the physiology of catabolism and its regulation, it is common practice to use colorimetric indicator plates to facilitate the isolation or identification of microbial strains. Conventionally, however, the color differences generated with the indicators are based on pH changes. That is, the color change that differentiates the microorganisms is based on the production or consumption of acid by the microorganisms. For this reason the method has primarily found utility in testing for microorganisms that catabolize a sugar or the like to produce acid. Hence, the utility is quite restricted in that it is not applicable to the numerous strains of microorganisms that are characterized by their ability to catabolize amino acids, fatty acids, or other types of compounds with no resultant production of acid or other cause for change in pH. Also, the colorimetric technique based on changes in pH can, in many instances, produce ambiguous results. For example, often the acidic compounds initially produced are then further oxidized thereby resulting in a gradual continued change in the pH and causing the color to fade. Further, since the change in color is predicated solely on change in pH and since the change in pH caused by the microorganisms is often only slight, the technique is satisfactory only where the total chemistry of the system is such that no changes in the pH can occur other than by way of the metabolic behavior of the microorganisms.

Briefly, what I have discovered is that a far more easily controlled, more sensitive, and less restrictive way to test and identify microorganisms is feasible by a composition wherein the change in color is predicated not on a change in pH and the pressure of a pH indicator but rather on an oxidation-reduction reaction which involves an oxidation-reduction indicator and which results from the catabolic behavior of the particular microorganism or type of microorganism for which the test is being made. More specifically, the preferred embodiments of the present invention involve a color change by way of the reduction of a tetrazolium compound to a formazan compound. The reducing agent causing the reduction reaction is or results from one or more of the catabolites produced during the catabolism of a test substrate compound included in the composition. Further, and more specifically with respect to the preferred embodiments of the present invention, the compositions used to identify or test the microorganism or strain of microorganism include: (1) a tetrazolium compound which undergoes a change in color upon reduction to a formazan compound, (2) a test substrate compound, i.e. a biodegradable compound which, if catabolized by the microorganism, will produce a catabolite engendering reduction of the tetrazolium compound; (3) a buffer to maintain the pH of the composition at a level which enables microorganism culture growth but which does not itself cause or prevent reduction of the tetrazolium compound to the colored formazan compound; and (4) nutrient for the microorganism or strain of microorganism in a concentration sufficient to induce culture growth without itself causing or resulting in reduction of the tetrazolium compound. Any one such composition is, by way of the particular test substrate compound it includes, useful for the colorimetric testing of a given microorganism or strain of microorganism. However, by using a series of such compositions, each with a different test substrate compound, a culture can be tested so as to identify the microorganism strain in the culture, this by way of the presence or absence of color changes in the various compositions in which the culture is allowed to grow. Hence, the invention further comprehends a test plate, or container, having separate recesses or compartments each of which contains a different such composition such that when a culture of unknown microorganism content is grown while in contact with each of the various compositions, there is indication of the particular microorganisms or microorganism strain in the culture by way of change in color or absence of change in color in the various compositions. The compositions can additionally contain some agar or the like to provide a gel or gel-like consistency for convenient growth of the microorganism cultures on the surface of the compositions.

Other details, features and advantages of the invention will appear more clearly from the following detailed description of preferred embodiments thereof made, in part, with reference to the drawings in which.

THE OXIDATION-REDUCTION COLORIMETRIC INDICATOR

Figure 1:
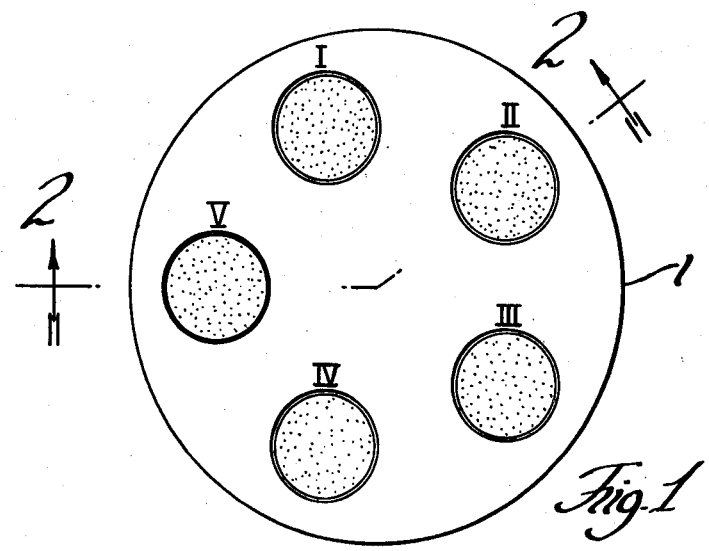
FIG. 1 is a top view of a test plate embodying the invention and useful for the convenient testing of a microorganism culture to indicate the particular microorganisms or strains of microorganisms present in the culture.

The oxidation-reduction colorimetric indicator included in the composition is a non-biodegradable compound that is substantially irreversibly reduced, with accompanying change in color, as a result of one or more of the catabolites produced by the microbial catabolism of the test substrate compound included in the composition. The preferred compounds for use as the colorimetric indicator are the tetrazolium compounds which are irreversibly reduced to form formazan with accompanying marked change in color. The tetrazolium compound used must, of course, be water soluble. The preferred tetrazolium compound is triphenyl tetrazolium chloride, i.e. 2,3,5-triphenyl tetrazolium chloride. The reduction reaction of the triphenyl tetrazolium chloride to the formazan compound is as follows:

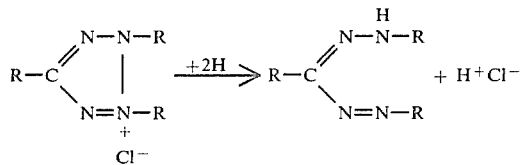

where R is a phenyl group. The triphenyl tetrazolium chloride is substantially colorless and the formazan compound precipitates out as red crystals. Hence, the reduction reaction is essentially irreversible. Other tetrazolium compounds satisfactory for the practice of the invention are exemplified by the following:

Tetrazolium violet, i.e. 2,5-diphenyl-3-a-napthyl tetrazolium chloride;

Neotetrazolium, i.e. 3,3'(4,4'-diphenylene)-bis (2,5-diphenyl) ditetrazolium chloride;

Blue Tetrazolium, i.e. 3,3'(4,4'-di-o-anisylene)-bis (2,5-diphenyl) ditetrazolium chloride;

Nitro Blue Tetrazolium, i.e. 3,3'(4,4'-di-o-anisylene)-2,2'-di(p-nitrophenyl)-bis (5-phenyl).

The concentration of the tetrazolium compound in the composition need not and preferably should not exceed about 0.1% by weight since with higher concentrations there can be inhibition of the microorganism culture growth. At the same time it is preferred that the concentration of the tetrazolium compound in the composition be at least about 0.0001% by weight since at lower concentrations the coloration resulting from the formation of the formazan compound upon reduction is too slight. Where triphenyl tetrazolium chloride is used a concentration of 0.0025% is ideal in most instances.

THE TEST SUBSTRATE

Before discussing the compounds which can be used as the test substrate it should be appreciated that the invention has utility not only for identifying the microorganism or type of microorganism present in a culture of unknown microorganism content, but also for studying and establishing the catabolic behavior of microorganisms of known identity. In the latter, cultures of the microorganism of known identity are tested with each of various compositions of the present invention, each composition containing a different test substrate, the results of each such test indicating whether the particular microorganism being tested does or does not catabolize the test substrate in the composition used for the test. By the use of a wide variety of test substrates the precise catabolic behavior of the microorganism can be established. The information so gained, along with all already-known information with respect to the catabolic behavior of the numerous and various microorganism strains, is, of course, useful for the practice of the invention for identifying the particular microorganism or type of microorganism present in a culture of unknown microorganism content. An example of such a culture is one grown from a sample drawn from a human patient, the purpose of the test being to identify the particular microorganism in the sample as an assist to the physician in treating the patient.

Hence, the test substrate included in the composition can be any of a variety of biodegradable compounds (i.e. catabolized by one or more microorganisms or strains of microorganisms), the catabolite or catabolites resulting from the catabolism being such as to engender the reduction of the tetrazolium compound to a formazan compound with the accompanying change in color.

To exemplify, the compound used as the test substrate can be selected from: the carbohydrates, including the sugars, both the monosaccharides and the polysaccharides, the starches and the celluloses; the long and short chain fatty acids as well as the other aliphatic acids, both monocarboxylic and polycarboxylic, and their salts and glycerides; the monohydric and polyhydric alcohols; the aliphatic aldehydes and ketones; the amino acids and the peptides; the aromatic compounds such as the purines, pyrimidines, ribonucleosides, benzoates, and catechols. The following specific compounds which have been used as the test substrate in the practice of the invention will serve to further illustrate: Maltose, D-glucose, L-fucose, D-ribose, lactose, D-fucose, ribitol, fumaric acid and salts, oleic acid and salts, propionic acid and salts, L-alanine, D and L-serine, L-proline, L-glycine, hydroxy-L-proline, L-valine, L-lysine, L-histidine, L-arginine, D-mannitol, D-gluconolactone, D-glucose-6-P, L-rhamnose, i-inositol, D-xylose, glycerol, lactic acid and salts, citric acid and salts, succinic acid and salts, maleic acid and salts, acetic acid and salts, butyric acid and salts, glutamic acid and salts, aspartic acid and salts, gluconic acid and salts, caproic acid and salts and glycerides, gentisic acid and m-hydroxy benzoic acid.

As indicated previously, the conventional colorimetric techniques used to test for microorganisms are dependent on pH changes and hence are generally useful only where the microorganism catabolizes sugar or other carbohydrate to generate acid. As distinguished from this, the compositions and methods of the present invention are useful not only as regards such microorganisms but also for identification or testing of microorganisms that catabolize other classes of organic compounds as illustrated by the above classes and specific examples of test substrates useful for the practice of the invention. The appropriate choice of a test substrate will be further illustrated by the specific example which will be given hereinafter.

It is preferred that the concentration of the compound used as the test substrate be at least about 2 millimols per liter, and the concentration used can range up to as high as 500 millimols per liter. The precise concentration used within this range determines the rate and extent of formazan formation and hence the rate and depth of color formation. In general, the higher the concentration of the test substrate compound the more rapid the color formation and the greater the depth of the color. However, there is seldom, if ever, need for a concentration of more than about 50 millimols per liter and a typical and preferred concentration for the test substrate compound is about 20 millimols per liter.

THE BUFFER

A buffer is included in the composition with two considerations in mind: (1) the buffer acts to maintain the pH of the composition so as to provide an environment suitable for good growth and prolonged viability of the microorganism; and (2) the buffer controls the pH of the composition so as to prevent excess alkali accumulation (which can itself cause colored formazan formation) or excess acid accumulation (which can prevent colored formazan formation). Taking into account both of these factors, the choice and concentration of the buffer generally should be such as to maintain the pH of the composition at from about 4.5 to 12.5, it being understood that the precise choice of pH to be maintained will depend on the particular tetrazolium compound being used and on the characteristics of the microorganism being tested. In general, a concentration of from about 50 to 500 millimoles per liter buffer is satisfactory.

In addition, it is important that the buffer selected should not contain compounds that the microorganisms being tested can catabolize; otherwise the buffer itself could engender reduction of the tetrazolium compound, thereby interfering with the test. Suitable for use as buffers are morpholino propane sulfonate, which is excellent, and the water soluble alkali metal and alkaline earth metal phosphates, carbonates and bicarbonates.

THE NUTRIENT

Just as in the case of the choice of the compound used as the test substrate, so also in the case of the nutrient, the precise choice must be predicated on the particular microorganism or strain of microorganism involved. Actually, the ideal nutrient would be one that supports rapid growth of all microorganisms; however, at present no such universally acceptable nutrient is known. Hence, as has been indicated, the choice of nutrient may vary from one composition to another, depending upon the microorganism or strain of microorganism for which the composition is intended. But as is well known by those skilled in the art, irrespective of the particular microorganism or strain of microorganism involved, it is always preferable, if not essential, that the nutrient include one or more compounds from each of the following groups: (1) sufficient amounts of the essential minerals for culture growth in utilizable form, for example, phosphate, sulfate, ammonia, potassium, sodium, calcium, iron, magnesium, manganese, and molybdenum; (2) amino acids including at least the twenty that are found in protein; (3) the purines and pyrimidines; and (4) the vitamins such as thiamin, biotin, pyridoxine, nicotinic acid, riboflavin, etc.

Other compounds that may be helpful to include are: unusual amino acids and amino acid-derivatives (e.g. D-amino acids, α-amino butyrate, β-alanine, taurine), peptides, gluthathione, mono- and polysaccharides, phosphorylated and aminated sugars, fatty acids, lipids, phospholipids, lecithins, polyamines, polyphosphates, ribo- and deoxyribonucleosides and nucleotides, carboxylic acids, alcohols, hemin, and quinones.

As is well known by those skilled in the art, nutrients which are close to the ideal, i.e. which are useful for a very wide range of microorganisms, are available on the market, examples being Proteose Peptone (useful, for example, at 0.2% by weight) and Tryptone (useful, for example, at 0.125% by weight) available from Difco, Inc. of Detroit, Mich. The following specific example is typical of the composition of a nutrient satisfactory for the practice of the present invention:

EXAMPLE OF NUTRIENT COMPOSITION OF BROAD APPLICABILITY

An aqueous solution containing: (a) 0.1 millimol per liter of each of the following L-amino acids or salts thereof: alanine, arginine hydrochloride, potassium aspartate, asparagine, cysteine hydrochloride, sodium glutamate, glutamine, glycine, histidine hydrochloride, isoleucine, leucine, lysine hydrochloride, methionine, phenylalanine, proline, serine, threonine, tryptophan, tyrosine, and valine; (b) 0.1 millimol per liter of each of the following purines and pyrimidines: adenine, guanine, uracil, cytosine, and thymine; (c) 0.01 millimol per liter of each of the essential vitamins as aforesaid; and (d) trace amounts of the minerals as aforesaid. Just the ordinary mineral contamination of the water and other ingredients used is generally sufficent to provide the mineral content required, except possibly for phosphate, sulfate, ammonia, potassium and magnesium, and to assure ample supply thereof the nutrient can include 0.1% by weight of each of potassium phosphate, magnesium sulfate and ammonium chloride. (The minerals can be supplied in whole or in part as the cation or anion of the buffer which is used.)

It is important to the practice of the present invention that the concentration of nutrient be low—sufficiently low that no one catabolizable organic ingredient of the nutrient be present in an amount of more than about one millimol per liter, and preferably about 0.1 millimol per liter. The importance of using a very low concentration of nutrient will be apparent from the fact that whereas the ideal nutrient would contain only ingredients totally assimilated by the microorganism, as a practical matter one or more of the ingredients of the nutrient will be such as can be catabolized by the microorganism. Hence, if the concentration of any such ingredient of the nutrient were high then the catabolism thereof by the microorganism would result in sufficient generation of catabolites as to falsify the test results by causing reduction of the tetrazolium compound albeit the particular microorganism could not catabolize the test substrate compound included in the composition. By maintaining the concentration of nutrient sufficiently low that no one catabolizable ingredient of the nutrient is present in an amount of more than 1 millimol per liter, and preferably about 0.1 millimol per liter, there is assurance that even though the nutrient ingredient is catabolized the amount of catabolite generated will not be sufficient to influence the test results. In general, the concentration of the nutrient should be such that no single catabolizable organic ingredient thereof is present in an amount of greater than about 1/100 of the amount of the test substrate compound included in the composition. Where the concentration of the test substrate compound is 20 millimols per liter and the nutrient concentration is such that no one catabolizable ingredient is present in an amount of more than about 0.1 millimols per liter, this provides a ratio of 1/200, which is very much on the safe side.

SPECIFIC EXAMPLE

To illustrate the invention, this example shows its use for differentiating among several species of Pseudomonas. *Pseudomonas fluorescens* can catabolize both inositol and mannitol. *Pseudomonas aeruginosa* can catabolize mannitol but not inositol. *Pseudomonas putida* can catabolize neither of these compounds. All three species can catabolize valine. Thus, the ability or inability of the species to catabolize these compounds (directly indicated by their ability or inability to effect a reduction of triphenyl tetrazolium chloride to the colored formazan compound when grown in an appropriate composition containing one of them) serves as the basis of a test to differentiate among the three Pseudomonas species.

Four compositions were prepared, all four containing: as the oxidation-reduction indicator, 0.0025% (by weight) triphenyl tetrazolium chloride; as a buffer to provide a pH of about 7, 0.7% $K_2HPO_4$, 0.3% $KH_2PO_4$, 0.01% $MgSO_4$; as a nutrient, 0.2% Proteose Peptone; as a gel former, 1.5% agar. As an alternative to the Proteose Peptone as a nutrient, there can be used the previously herein disclosed example of a nutrient composition of broad utility, the concentration being such as described in the discussion relative to the nutrient.

One composition, designated as composition A, consisted of the above with no other addition and simply served as the "negative control" to assure that none of the aforesaid ingredients could cause color formation.

To another of the compositions, designated as composition B, there was added mannitol in an amount to provide a concentration of about 20 millimols per liter.

To the third of the compositions, designated as composition C, there was added inositol in an amount to provide a concentration of about 20 millimols per liter.

To the last of the compositions, designated as composition D, there was added valine in an amount to provide a concentration of about 20 millimols per liter, this composition serving as the "positive control".

Pure liquid cultures were grown of each of the three species designated: *P. fluorescens* PF014; *P. aeruginosa* PA038; and *P. putida* A.3.12.

Four plates were prepared, each containing one of the four compositions and carrying the designation of the composition, i.e. plates A, B, C, and D. All four compositions were the same in color—a slightly yellowish white.

Each of the three liquid cultures was then streaked onto each of the four plates to provide isolated colonies on each of the plates.

Results: none of the three colonies on plate A, the negative control plate, caused any change in color. On plate B each of the *P. fluorescens* and *P. aeruginosa* colonies carried a change in color to red whereas the *P. putida* colony caused no change in color. On plate C the *P. fluorescens* colony caused a change in color to red whereas neither the *P. aeruginosa* nor the *P. putida* colony caused any change in color. On plate D, the positive control plate, colonies of all three species caused a change in color to red.

From the aforesaid example it will be manifest that if a culture were known to contain Pseudomonas of one or another of the three strains but with the precise strain not being known, the invention could be used to identify the precise strain. Using the compositions of the invention, as aforesaid, if the strain turned red when grown in both inositol and mannitol, it would be classified as *P. fluorescens*. If the strain turned red when grown in mannitol but not inositol, it would be classified as *P. aeruginosa*. If the strain failed to turn red when grown in either mannitol or inositol, it would be classified as *P. putida*.

In this specific example separate plates were used for carrying the compositions. However, as will be illustrated by the further example and discussions which follows, it is generally preferred for testing convenience and procedure that a single compartmentalized plate or other container be used, each compartment containing a different composition, in accordance with the invention, isolated from the others.

FURTHER AND MORE GENERALIZED EXAMPLE OF THE PRACTICE OF THE INVENTION

One of the classes of microorganisms quite commonly encountered in medical diagnostic, treatment and research work is *Salmonella typhimurium*. Also is well known to those in the field of microbiology, there are numerous strains of *Salmonella typhimurium* and considerable work has already been done and is reported in the literature with respect to the catabolic behavior of each of a number of the strains. For purposes of this example of the practice of the present invention it will be assumed that the specimen to be tested and identified contains one or the other of six different strains or species of *Salmonella typhimurium* which will here simply be designated as Strains 1 through 6.

Strain 1 is known to catabolize d-xylose, L-rhamnose and m-tartrate, but is known not to catabolize m-inositol.

Strain 2 is known to catabolize d-xylose, m-inositol and m-tartrate, but is known not to catabolize L-rhamnose.

Strain 3 is known to catabolize d-xylose, m-inositol and L-rhamnose, but is known not to catabolize m-tartrate.

Strain 4 is known to catabolize m-inositol and L-rhamnose, but is known not to catabolize d-xylose or m-tartrate.

Strain 5 is known to catabolize d-xylose and m-tartrate, but is known not to catabolize m-inositol or L-rhamnose.

Strain 6 is known to catabolize m-inositol and m-tartrate, but is known not to catabolize d-xylose or L-rhamnose.

Hence, the four test substrate compounds to be used in the practice of the present invention for identification of the particular species of *Salmonella typhimurium* from amongst the six species are d-xylose, m-inositol, L-rhamnose, and m-tartrate. These test substrate compounds, and the compositions containing them, will here be designated as I, II, III, and IV, respectively, the designation V to be used for a negative control composition, i.e. a composition otherwise the same as the others except containing no test substrate compound.

The aforesaid catabolic behavior of the six species or strains is outlined in the following table:

| | *Salmonella Typhimurium* Catabolizes: | | | |
|---|---|---|---|---|
| Strain | I<br>d-xylose | II<br>m-inositol | III<br>L-rhamnose | IV<br>m-tartrate |
| 1 | yes | no | yes | yes |
| 2 | yes | yes | no | yes |
| 3 | yes | yes | yes | no |
| 4 | no | yes | yes | no |
| 5 | yes | no | no | yes |
| 6 | no | yes | no | yes |

In accordance with the invention five compositions are prepared, each of these compositions containing a tetrazolium compound, a buffer and a nutrient in accordance with the aforesaid teachings. More specifically, the compositions, as regards the tetrazolium compound, the buffer and the nutrient, can be the same as indicated in the previous specific example with respect to use of the invention for differentiating between species of Pseudomonas. It will be understood, of course, that as regards all ingredients other than the test substrate compound, all five compositions are identical.

Figure 2:
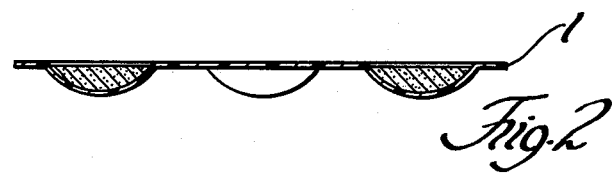
FIG. 2 is a view taken on the line 2—2 of FIG. 1.

Composition I additionally contains about 20 millimols per liter d-xylose, composition II additionally contains about 20 millimols per liter m-inositol, composition III additionally contains about 20 millimols per liter L-rhamnose and composition IV additionally contains about 20 millimols per liter m-tartrate (neutralized). Composition V is simply used as a negative control and hence contains nothing additional—contains no test substrate compound. Referring to FIGS. 1 and 2, there is shown a plate 1 which can be of any suitable material such as glass or biologically inert organic plastic, having five compartments isolated from each other and taking the form of five wells designated I–V. These five compartments I–V contain the five compositions aforesaid of like designation.

A culture of the *Salmonella typhimurium* to be tested is placed in each of the five compositions and allowed to grow therein. Thereupon, identification of the particular species or strain can be made on the basis of which of the compositions remain white and which of the compositions develop a coloration (red if triphenyl tetrazolium chloride is used) in accordance with the following table:

| Strain | I | II | III | IV | V |
|---|---|---|---|---|---|
| 1 | red | white | red | red | white |
| 2 | red | red | white | red | white |
| 3 | red | red | red | white | white |
| 4 | white | red | red | white | white |
| 5 | red | white | white | red | white |
| 6 | white | red | white | red | white |

Hence, if, for example, I and IV, along with composition V, remain white whereas compositions II and III develop coloration, then the strain is identified as strain 4.

Whereas only six strains are dealt with in this example, it will be manifest that by using additional compositions, each containing a different test substrate compound, provision can be made for the possibility of other strains, it only being necessary that for each strain involved the catabolic behavior be different from all other strains with respect to some one compound or another.

While not essential, it is always preferable to use a negative control composition since if the negative control composition develops a red coloration, then the results of the total test are suspect. A positive control composition is of lesser importance though desirable where practical.

The aforesaid examples are illustrative of the use of the invention where the specimen to be tested is of known microbial content, at least to some extent. Further within the purview of the invention, however, is the use of a series of test plates, each containing a plurality of compositions distinct from each other by way of the test substrate compound included and with an early plate or plates in the series being for general, or relatively general, identification of the microorganism strain, or its catabolic behavior, and with later plates in the series being for more specific identification of the microorganism or its catabolic behavior. For example, the first test plate in the series can have compositions containing test substrate compounds which are quite different from each other and then with later plates in the series having compositions with test substrate compounds similar to each other. Alternatively, a single plate or other container having a large number—as many as hundreds—of different compositions can be used so that with but a single test a great amount of information can be gained with respect to the catabolic behavior or identification of the test specimen.

Figure 3:
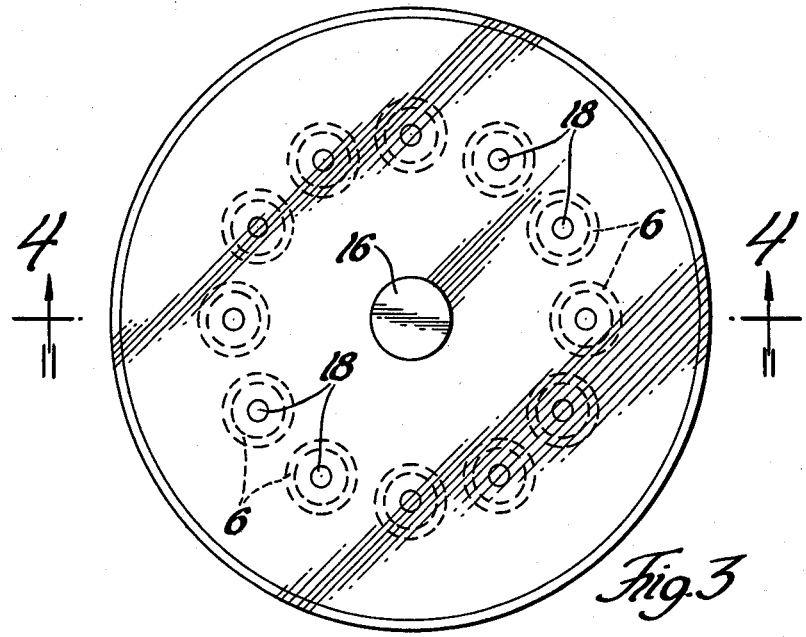
FIG. 3 is a top view of another embodiment of the invention.
Figure 4:
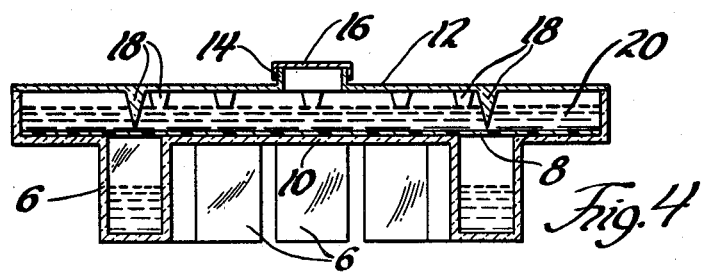
FIG. 4 is a side view in section, taken on line 4—4 of FIG. 3.

In this regard, reference is now made to FIGS. 3 and 4 which show a test container embodying, and for the convenient practice of the method of, the present invention. The container shown has a bottom portion of a molded, biologically inert, transparent organic resin having a plurality of downwardly extending compartments 6 which are isolated from each other and which, in the particular embodiment shown, are circumferentially arranged and spaced from each other. Each of the compartments 6 is partially filled with a composition which includes the oxidation-reduction indicator and a test substrate compound, in accordance with the invention, but with each composition differing from the others by way of the test substrate compound it contains. The compartments 6 are sealed from each other and from the upper part of the container by a liquid impermeable, biologically inert, organic resin membrane 8 which is sealed to the flat wall 10 which constitutes the floor of the container from which the compartments 6 extend. The upper portion of the container comprises a lid 12 of a biologically inert, relatively flexible and preferably transparent organic resin having an opening 14 sealed by a removable cap 16. The lid is further provided with a plurality of circumferentially spaced, downwardly extending pointed projections 18, each projection being immediately above one of the compartments 6. The upper portion of the container, above the membrane 8, is partially filled with an aqueous solution 20 containing nutrient and buffer for microorganism culture growth, the amount of nutrient and buffer being as taught previously herein. The cap 16 sealing the opening of the container is such as to be easily removable for introducing a specimen of the microorganism to be tested into nutrient solution 20. The membrane 8 functions as a barrier to entry of the microorganism into the compartments 6 until it is breached. That is, membrane 8 is such as to be easily punctured by the pointed projections 18 upon the application of downward pressure to the flexible lid 12. Hence, until downward pressure is applied to the lid 12, the aqueous compositions in the compartments 6 are isolated by the membrane 8 from the liquid 20 whereas after downward pressure is applied to the lid 12 so as to cause puncture of the membrane 8 by each of the projections 18, the liquid 20 can flow through the punctures into each of the compartments 6. After the puncturing the lid flexes up to its normal position. In use, the microorganism specimen to be tested is introduced into the nutrient liquid 20 by removing the cap 16 (the cap 16 being resealed after introduction of the specimen) and, after the culture is allowed to grow in the nutrient liquid, the flexible lid 12 is depressed thereby to puncture the membrane portions above each of the compartments 6 and hence allowing the culture to flow through the resulting punctures into the compartments 6 and hence into contact with each of the various compositions containing the different test substrate compounds. Since until puncture the membrane 8 seals all of the compartments 6 from each other and from nutrient liquid 20, the compositions in the compartments can be in liquid form and hence need contain no agar or other gelling agent—though agar or other gelling agent can be included if desired. The container itself can be printed with identification of the test substrate compound included in each of the compartments or alternatively, of course, the container can simply carry a numerical or the like designation for each of the compartments and be accompanied by a printed list specifying each of the various compositions. As indicated previously, it is preferable that one of the compositions be a negative control, i.e.

contain no test substrate compound. After the culture grown in the nutrient liquid is admitted to the various compartments by puncture of the membrane 8 as aforesaid, test results are indicated by the development or lack of development of color in each of the various compartments as can be easily viewed through the transparent container. If desired, nutrient and buffer can be initially included in the compositions in the compartments, or the supply of these ingredients can be solely by way of the aqueous nutrient and buffer solution 20 in the upper part of the container. It will, however, be understood that, in any case, at the time of culture growth in the compartments the compositions in the compartments do contain all four of the essential ingredients for the test, as herein taught, save only for the negative control composition (if one is used) which does not contain test substrate compound.

As has already been indicated, the above compositions and methods provide a generalized test for microorganisms rather than just a test specific for one particular type of microorganism. However, I have discovered and established that when the microorganism being tested is anaerobic and hence cannot be cultured in the presence of oxygen, a significant improvement in the compositions and method can be accomplished by including a further ingredient, as will now be described. But before proceeding, it should be noted that in the aforesaid I have disclosed a preferred embodiment of the invention wherein the microorganism being tested is first cultured in a solution of just nutrient and buffer and then, after being so cultured, the culture which results is admitted into the solution of the oxidation-reduction indicator and test substrate. To exemplify, in the preferred embodiment of the method described with reference to FIGS. 3 and 4, the microorganism to be tested is first cultured in a solution, above the membrane 8, containing the nutrient and buffer and then the resulting microorganism culture is admitted into the various solutions of test substrate and oxidation-reduction indicator in the compartments below the membrane.

What I have found is that in all cases, and particularly where the microorganism being tested is anaerobic, it is preferable that the microorganism be present in the nutrient solution at a culture density of about $2 \times 10^8$ cells (i.e. microorganisms) per milliliter, at the time the nutrient solution containing the culture is added to the solution or solutions of oxidation-reduction indicator and test substrate.

Of course it is manifest that the nutrient solution used for growing anaerobic microorganisms must be free of oxygen, i.e. $O_2$. What I have found is that in the practice of my method for identifying or testing anaerobic microorganisms, the nutrient solution used can be effectively purged of oxygen by the inclusion of any of a wide variety of compounds which will reduce oxygen but yet which will not affect the oxidation-reduction indicator. Additionally, the compound must, of course, be non-toxic to the microorganism and it must be a compound which is not catabolized by the microorganism. A preferred such compound is glutathione which is not catabolized by, nor toxic to, at least most anaerobic microorganisms and which will reduce oxygen but yet not reduce triphenyl tetrazolium chloride so long as any $O_2$ is present, leastwise not at a pH of about 8 or less. Other compounds which qualify because of their reducing properties are ascorbic acid (it will be understood that where an acid is specified, it can also be used as a salt, and vice versa), thiomalic acid, thioglycolic acid, cysteine, sodium formaldehyde sulfoxalate, thiodiglycol, dithioerythritol, sodium sulfite or bisulfite, and sodium dithionite. Of course, in all instances the compound selected cannot be one which is catabolized by the particular anaerobic microorganism involved, though the compound can function additionally as a nutrient for the microorganism. Glutathione, for example, functions not only to purge oxygen by reducing it to water, but also as a nutrient. However, whether the compound be the generally preferred glutathione or any of the other numerous qualified compounds, it must be present in a concentration sufficiently high to reduce all $O_2$ in the nutrient solution to which it is added. To assure against the presence of any oxygen (i.e. $O_2$) it is preferred that the compound used for affecting a reduction of the oxygen be added to the solution in an amount to provide a concentration of at least about 5 millimoles per liter. No more than about 10 millimoles per liter is generally required.

In addition to the inclusion of a compound, as immediately aforesaid, for reducing oxygen in the solution there are other inclusions which are also desirable where the microorganism being tested is anaerobic. One such further inclusion is that of a compound for supplying carbon dioxide to the solution since, in general, anaerobic microorganism culture growth is favored by the presence of carbon dioxide. Ammonium bicarbonate is generally preferred though other carbonates (i.e. either carbonates or bicarbonates) which are soluble in the solution at its pH can be employed instead of ammonium bicarbonate. The pH preferred for the culturing and testing of anaerobic microorganisms is from about 4.5 to 8.

As is well known in the art, anaerobic microorganisms require a higher nutrient concentration than do aerobic microorganisms in order to undergo culture growth to a comparable yield. This is especially true with respect to sugar or other carbohydrate in the nutrient solution. Hence, in the example which will be given below, glucose is included in an amount of 2.5 millimoles per liter. This relatively high concentration of glucose in the nutrient solution has not interfered with the test results with any of the classes of anaerobic microorganisms tested thus far—which classes are mentioned hereinafter. Of course if this amount of glucose does engender reduction of the indicator, then the glucose can be eliminated, or its concentration greatly reduced, and replaced by one or a combination of other carbohydrates in an amount, or amounts, sufficiently low as to function only as a nutrient. In this regard it should again be pointed out that it is always preferred that the hereinbefore described positive and negative test controls, especially the latter, be used to assure the validity of the test results.

The following specific example will serve to illustrate.

An aqueous nutrient solution is made up to contain the following ingredients in the concentrations indicated:

| Ingredient | Concentration |
| --- | --- |
| $K_2HPO_4$ | .7% (by weight) |
| $KH_2PO_4$ | .3% |
| $MgSO_4$ | .01% |
| Proteose Peptone | .2% |
| Hemin | 2 micrograms/ml |
| ammonium bicarbonate | .1% |
| glucose | 2.5 millimoles/l |

| Ingredient | Concentration |
|---|---|
| glutathione | 8 millimoles/l |

If this nutrient solution is made up much in advance of its use, it is best that the glutathione be added only immediately before use since otherwise the glutathione could be depleted by continued dissolving of atmospheric oxygen into the solution. In all cases it is desirable that the nutrient solution be kept in a capped container, both prior to and during use in culturing the microorganism, and with minimum air in the container above the solution.

This nutrient solution, typically 10 milliliters thereof in a capped tube, is innoculated with a colony of the microorganism to be tested. Culture growth is allowed to continue in the nutrient until the culture density is about $2 \times 10^8$ cells per milliliter. Such a culture density is generally obtained within about 16 hours incubation at a temperature of about 35° to 40° centigrade.

In the meantime the solutions of substrate compounds and oxidation-reduction indicator to be used for the testing are made up and are placed in a series of tubes. The tubes used should preferably be of relatively small diameter. Tubes having a diameter of 12 millimeters and a length of 100 millimeters are quite satisfactory. The concentrations of the oxidation-reduction indicator, preferably triphenyl tetrazolium chloride, and test substrate compounds can be as herein previously described.

Simply for purposes of further detailed description of a preferred method for testing anaerobic microorganisms, it will be assumed that the test is to be run using four different test substrate compounds.

Prior to or during growth of the anaerobic microorganism culture in the nutrient solution as described, a rack of six of the 12 mm by 100 mm tubes is set up. To each of four of these tubes is added a different one of the test substrate compounds in the form of 0.1 ml of a 10% aqueous solution thereof. To the fifth tube there is added simply 0.1 ml of water, this to be the negative control test solution. To the sixth tube there is added 0.1 ml of a solution containing 10% of all four of the test substrate compounds, this to be the positive test control. It should be noted that none of these solutions nor the water in the negative control test nor the solution of triphenyl tetrazolium chloride to be added (infra.) are purged of $O_2$ and hence do contain some dissolved $O_2$.

To each of these tubes is added 1 ml of the nutrient solution containing the suspended anaerobic microorganism cultured to a culture density as described, plus 0.025 ml of an approximately 0.1% triphenyl tetrazolium chloride solution so that the final concentration of the triphenyl tetrazolium chloride in the total mix is approximately 0.0025%. The tubes, uncapped or loosely capped, are incubated for about one hour at about 35° to 40° C. The tubes containing test substrate compounds catabolizable by the microorganism will turn red while those containing non-catabolizable test substrate compounds will remain uncolored. Particularly where the test substrate compound is not a sugar or other carbohydrate, if the red color does not develop within one hour, incubation should be continued at least somewhat beyond one hour since catabolizable test substrate compounds which are not carbohydrates are generally slower to be catabolized than are the carbohydrates. Of course if the negative test control develops a red color, then the test results are not valid and the need for reformulation of the nutrient solution is indicated. Should none of the six tubes develop a red color, not even that containing the positive test control solution, then the test results may or may not be valid and final determination on this can be made by running the test using other test substrate compounds.

I have now used this method to test *B. fragilis, B. thetaiotaomicron, C. perfringens,* and *F. varium*. The test results I have obtained are substantially in agreement with those obtained using conventional methods, (i.e. a pH indicator); but with my test method providing greater speed and sensitivity and not being limited only to the use of test substrate compounds which affect pH when catabolized.

It will be understood that in preparing the suspension of the microorganism in the nutrient solution for the practice of the method, the microorganism culture can be grown entirely in the nutrient solution in which it is suspended at the time of the test, of it can be entirely grown or at least initially grown otherwise, as on a plate in agar, and with the colony then being suspended in the nutrient solution for any further growth that might be necessary to attain the desired culture density, and for testing.

Hence, while the invention has been described specifically with reference to preferred embodiments thereof, various changes and modifications may be made all within the full and intended scope of the claims which follow.

What is claimed is:

1. A method for identifying or testing a microorganism comprising preparing a suspension of a culture of the microorganism in a nutrient solution to a culture density of about $2 \times 10^8$ cells/ml, and then bringing said suspension into contact with an aqueous solution containing an oxidation-reduction indicator which substantially irreversibly undergoes a change in color upon being reduced and a biodegradable test substrate compound which, when catabolized by a microorganism, will engender reduction of the indicator, the concentration of nutrient in said suspension being insufficient to engender reduction of the indicator when said suspension contacts said solution, said suspension containing a compound which reduces $O_2$ but which does not reduce the oxidation-reduction indicator and which is present in said suspension in an amount sufficient to reduce all the $O_2$ therein, at least one of said suspension and said solution containing a buffer to maintain the pH at from about 4.5 to 8 while said suspension is in contact with said solution.

2. A method for identifying or testing a microorganism comprising preparing a suspension of a culture of the microorganism in a nutrient solution to a culture density of at least $2 \times 10^8$ cells/ml, said suspension having a pH from about 4.5 to 8 and being substantially sealed from the ambient atmosphere, and then unsealing and bringing said suspension into contact with a solution which is exposed to oxygen from the ambient atmosphere, which has a pH of from about 4.5 to 8, and which contains an oxidation-reduction indicator which substantially irreversibly undergoes a change in color upon being reduced and a biodegradable test substrate compound which, when catabolized by a microorganism, will engender reduction of the indicator, the concentration of the nutrient in said suspension being insufficient to engender reduction of the indicator when said suspension contacts said solution, said suspension containing a compound which reduces $O_2$ but which does not reduce the oxidation-reduction indicator at a pH of from 4.5 to 8 in the presence of $O_2$, said compound which reduces $O_2$ being present in said suspension in an amount sufficient to reduce all the $O_2$ therein.

3. A method as set forth in claim 2 wherein said oxidation-reduction indicator is triphenyl tetrazolium chloride and wherein said compound which reduces $O_2$ is glutathione and is present in said suspension in an amount of at least about 5 millimoles per liter.

* * * * *